United States Patent [19]

Kasdan et al.

[11] 4,093,866

[45] June 6, 1978

[54] DIFFRACTION PATTERN AMPLITUDE ANALYSIS FOR USE IN FABRIC INSPECTION

[75] Inventors: Harvey Lee Kasdan, Van Nuys; Donald Carleton Mead, Granada Hills, both of Calif.

[73] Assignee: Greenwood Mills, Inc., Greenwood, S.C.

[21] Appl. No.: 806,827

[22] Filed: Jun. 15, 1977

Related U.S. Application Data

[63] Continuation of Ser. No. 673,887, Apr. 5, 1976, abandoned.

[51] Int. Cl.$^2$ ............................................ G01N 21/32
[52] U.S. Cl. .................................. 250/563; 250/572; 250/578; 356/200
[58] Field of Search .................. 250/214 R, 562, 563, 250/572, 578; 356/199, 200, 205, 206, 209, 212, 202, 203; 350/6, 7

[56] References Cited

U.S. PATENT DOCUMENTS

| | | | |
|---|---|---|---|
| 3,618,063 | 11/1971 | Johnson | 250/563 |
| 3,908,118 | 9/1975 | Micka | 250/572 |
| 3,980,891 | 9/1976 | Slaker | 356/200 |

*Primary Examiner*—David C. Nelms
*Attorney, Agent, or Firm*—Cushman, Darby & Cushman

[57] ABSTRACT

A technique is provided for analyzing the shape of the amplitude envelope of a diffraction pattern's first order side lobe resulting from passing coherent light through a fabric material. The light intensity of the lobe is scanned from one side of the lobe to the other by a linear photo-diode array to provide successive voltage signals whose respective voltage values are a function of the light intensity at successively spaced increments from one side of the lobe to the other. Each of these successive voltage signals are compared with a series of reference voltages of substantially less number than the number of spaced increments, each reference voltage having a value greater than the value of the preceding reference voltage in the series to define a voltage range encompassing the highest voltage in the series of voltage signals. A numerical count is then provided of those voltage signals which have voltage values falling between the values of adjacent reference voltages in the series of reference voltages so that a plurality of counts is provided which indicates the amplitude distribution of light in the light lobe. The plurality of counts is substantially less in number than the number of spaced increments thereby reducing storage data requirements in the analysis of the amplitude envelope of the light lobe. Successive first order side lobes developed by successively passing the light beam through different areas of the fabric to cover a large area are analyzed to provide a succession of the pluralities of counts.

14 Claims, 10 Drawing Figures

DIFFRACTION PATTERN AMPLITUDE ANALYSIS FOR USE IN FABRIC INSPECTION

This is a continuation, of application Ser. No. 673,887 filed Apr. 5, 1976 which was abandoned upon the filing hereof.

This invention relates to a method and system for the rapid analysis of the shape of the amplitude envelope of a light lobe and more particularly to the analysis of first order side lobes in a diffraction pattern developed from a coherent light beam used in inspecting materials, such as fabrics manufactured in textile mills.

BACKGROUND OF THE INVENTION

In the Mead et al copending U.S. patent application Ser. No. 660,652 filed Feb. 23, 1976 and entitled METHOD FOR AUTOMATIC FABRIC INSPECTION, assigned to the same assignee as the present invention, there is disclosed a basic method of fabric inspection by analysis of the diffraction pattern developed from passing a coherent light beam through fabric material. In accord with that method, the height and shapes of side lobes developed in various regions of the diffraction pattern are compared to given references representative of a "good" quality of fabric. A grade count can thus be assigned to any fabric being inspected.

In the Fomenko copending patent application Ser. No. 660,653, now U.S. Pat. No. 4,057,351, filed Feb. 23, 1976 and entitled COHERENT SCANNING SYSTEM FOR FABRIC INSPECTION, also assigned to the same assignee as the present invention, there is disclosed a scanning system enabling high speed automatic inspection of large fabric areas to be carried out by the method disclosed in the first-mentioned copending application. Basically, this scanning system includes a scanning mirror which, through various optical components, causes the coherent beam to scan across the width of the fabric from one edge to the other. A descanning mirror has directed towards it the beam as it passes through successive areas across the width of the fabric, the descanning mirror then directing the coherent beam to appropriate detector optics.

In the Fomenko copending patent application Ser. No. 662,955, now U.S. Pat. No. 4,070,114, filed Mar. 1, 1976, entitled DETECTOR OPTICS FOR USE IN FABRIC INSPECTION, again assigned to the same assignee as the present invention, there are disclosed details of a preferred detector optics system enabling the simultaneous and individual analysis of each of the various first order side lobes developed in the diffraction pattern. The detector optics makes use of a linear photo-diode array for each first order side lobe of light to be analyzed and towards this end, the detector optics includes an optical squeezing means such as a cylindrical lens for squeezing the light lobe into a focused array of light for accommodation within the linear photo diode array. This squeezing not only removes elongation of the lobe as a result of astigmatic conditions all as explained in the last mentioned copending patent application but further results in a light intensity distribution along the diodes of the array such that voltage signals can be developed by scanning the light lobe from one side to the other by means of the array which signals are functions of the changing light intensity along the array.

The analysis of a lobe of light by a linear photo diode array is known in the art. For example, one such type of linear diode array is produced by the Reticon Corporation of Mountain View, California and is referred to by the registered trademark RETICON. These devices are referred to as self-scanning arrays in that they will successively analyse a light lobe from one side of the lobe to the other by "scanning" of the same. Equipment utilizing such linear photo-diode arrays for analysis are often referred to as video systems.

In many applications, diffraction pattern analysis in particular, the "shape" of a video signal contains implicitly or explicitly the information necessary to decide among alternative actions. In the conventional video systems there are typically necessary 500 or more picture elements (pixels) per scan line. If all pixels must be used in a processing system to determine an action decision, the rate these decisions can be made is necessarily limited. If additionally the location of the pertinent information is not fixed along the scan line, additional processing must take place.

Systems for analyzing the output data from linear photo diode arrays are known. For example, such systems are used for pulse height analysis in the nuclear field. Essentially, such pulse height analyzers utilize an analog peak detect and hold circuit on the common video of the linear photo diode array. The analog peak detect and hold circuits are very difficult to design for very short duration pulses. Further, they generally employ capacitors which must be discharged before measuring the next pulse.

As a consequence of all of the foregoing, the necessary extremely rapid inspection of fabric material in accord with the teachings set forth in the heretofore mentioned copending applications cannot readily be carried out with the prior art systems.

BRIEF DESCRIPTION OF THE PRESENT INVENTION

Bearing the foregoing in mind, the present invention has to do specifically with a method and system for the extremely rapid analysis of a light lobe and more particularly of a first order side lobe in a diffraction pattern developed by coherent light passing through fabric material in a fabric inspection system.

Basically, the technique of the present invention reduces the number of data values to be processed by a substantial amount while still maintaining the relevant information. Moreover, the technique completely eliminates the need for an analog type of pulse height detection and hold circuit, thereby vastly increasing the speed of analysis so essential if a practical fabric inspection system is to result.

Essentially, the method of analyzing the shape of the amplitude envelope of a light lobe in accord with the present invention includes the steps of scanning the light intensity of the lobe from one side of the lobe to the other to provide successive voltage signals whose respective voltage values are a function of the light intensity at successively spaced increments from the one side to the other. A series of reference voltages is provided of substantially less number than the number cf spaced increments, each reference voltage having a value greater than the value of the preceding reference voltage in the series to define a voltage range encompassing the highest voltage in the series of voltage signals. Each successive voltage signal in turn is compared with all of these reference voltages simultaneously and a numerical count of those voltage signals which have voltage values falling between the values of adjacent reference voltages in the series of reference voltages is provided. A plurality of counts thus results which indicates the amplitude distribution of light in the light lobe. These plurality of counts is substantially less in number than the number of spaced increments thereby reducing storage data requirements in the analysis of the amplitude envelope of the light lobe and further enabling a very rapid analysis.

A further important feature of this invention involves the steps of analyzing a series of successive light lobes, each in accordance with the above-described method to provide successive pluralities of counts. The mean values of these successive pluralities of counts is computed and subsequent pluralities of counts are then referenced to the mean values such that deviations by a given amount of one of the successive pluralities of counts from the mean values indicates a change in the amplitude envelope of that successive light lobe characterized by said one of the subsequent pluralities of counts. In the case of high speed fabric inspection, such deviation may be utilized to signal a defect.

The system for carrying out the foregoing method includes comparators provided with the reference voltages and connected to receive the voltage signals from a linear photo diode array together with latch means and appropriate counters. The use of latch means completely eliminates the need for an analog peak detect and hold circuit characteristic of the prior art and results in a vastly superior approach in the analysis technique.

BRIEF DESCRIPTION OF THE DRAWINGS

A better understanding of this invention as well as many further features and advantages thereof will be had by referring to the accompanying drawings in which.

DETAILED DESCRIPTION OF THE PREFERRED EMBODIMENT

The method and system for analysing the shape of the amplitude envelope of a light lobe in accord with the present invention has its preferred application in a high speed analysis of the diffraction pattern developed by passing coherent light through fabric such as textile material in an automatic inspection system and for purposes of the present application will be described in this respect. It should be understood, however, that the techniques can be used in other situations wherein the analysis of a lobe of light is desired.

Figure 1:
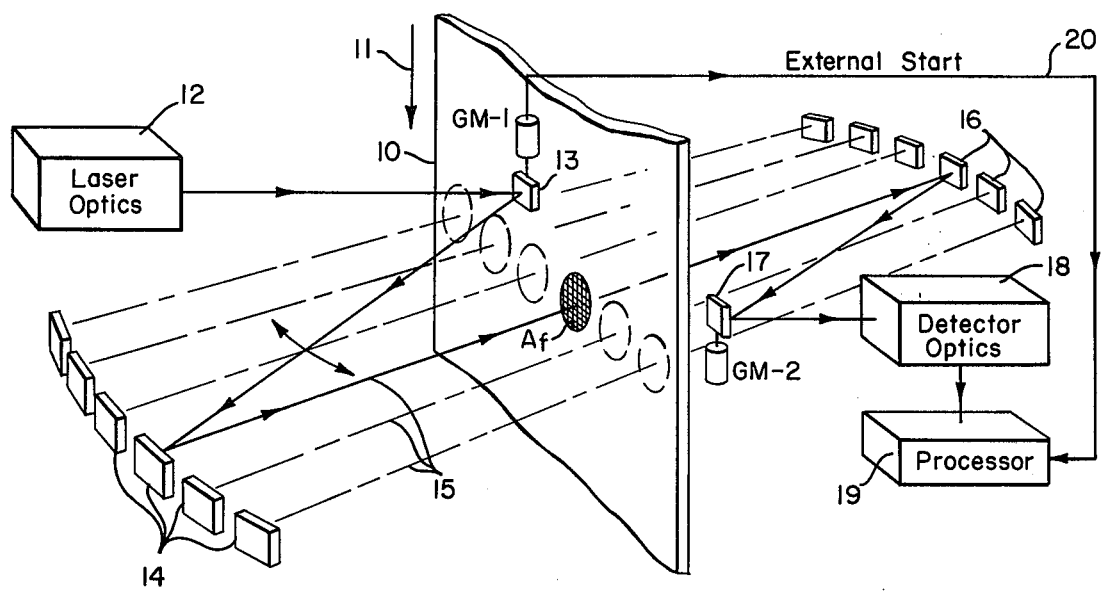
FIG. 1 is a highly diagramatic showing of a scanning arrangement for fabric inspection resulting in the development of diffraction patterns to be analyzed in accord with this invention.

Referring first to FIG. 1, there is shown a simplified system for high speed inspection of fabric by scanning the fabric from one edge to the other by a coherent light beam to develop successive diffraction patterns for analysis. Thus, the fabric is shown at 10 and is caused to move downwardly in the direction of the arrow 11 at a relatively high speed; for example, 120 yards per minute. The fabric 10 itself may be four feet across.

As described in the heretofore referred to copending patent application entitled COHERENT SCANNING SYSTEM FOR FABRIC INSPECTION, a coherent light beam is provided by appropriate laser optics 12 and directed towards a scanning mirror 13 also designated GM-1. The reflected light from the mirror 13 passes through fold mirrors (not shown) to eventually be directed by a plurality of mirrors 14 in parallel paths or channels 15, successively through the fabric 10. One such light channel is shown in solid lines passing through an area of the fabric designated Af to the other side.

A plurality of detecting mirrors 16 (there again being provided folding mirrors not shown) directs the successively received light to a descanning mirror 17 also designated GM-2. The light from the descanning mirror 17 passes to a detector optics designated by the block 18 and fully described in the referred to copending patent application entitled DETECTOR OPTICS FOR USE IN FABRIC INSPECTION. The output from the detector optics 18 passes to a processing system designated by the block 19 which constitutes the heart of the present invention.

It will be appreciated from the foregoing that a succession of diffraction patterns are developed by the coherent light beam as it passes through successive areas across the fabric 10 while the fabric itself is moving downwardly. The rate of downward movement is correlated with the scanning speed of the scanning mirror so that complete coverage of the fabric is assured.

In the simplified showing of FIG. 1, it will be noted that the successive areas from the light channels are spaced across the width of the fabric. In the actual scanning system used and as described in the referred to copending application, a similar arrangement is provided to pass the coherent beam from the far side of the fabric back through the fabric to fill in the intermediate spaces between the successive areas.

Regardless of the particular type of scanning system, it will be appreciated that there is provided at the processor 19 in extremely rapid succession a series of diffraction patterns individual regions of which are to be analyzed. The analysis of each diffraction pattern is carried out in a time sequential manner, each such pattern being treated individually and towards this end, an external start signal must be provided to the processor corresponding to the point in time that one of the successive areas of irradiation of the fabric 10 takes place. This external start signal in the example shown in FIG. 1 is generated by the scanning mirror 13 as it successively passes through positions which cause the successive areas to be irradiated, and passed on line 20 to the processor block 19.

Figure 2:
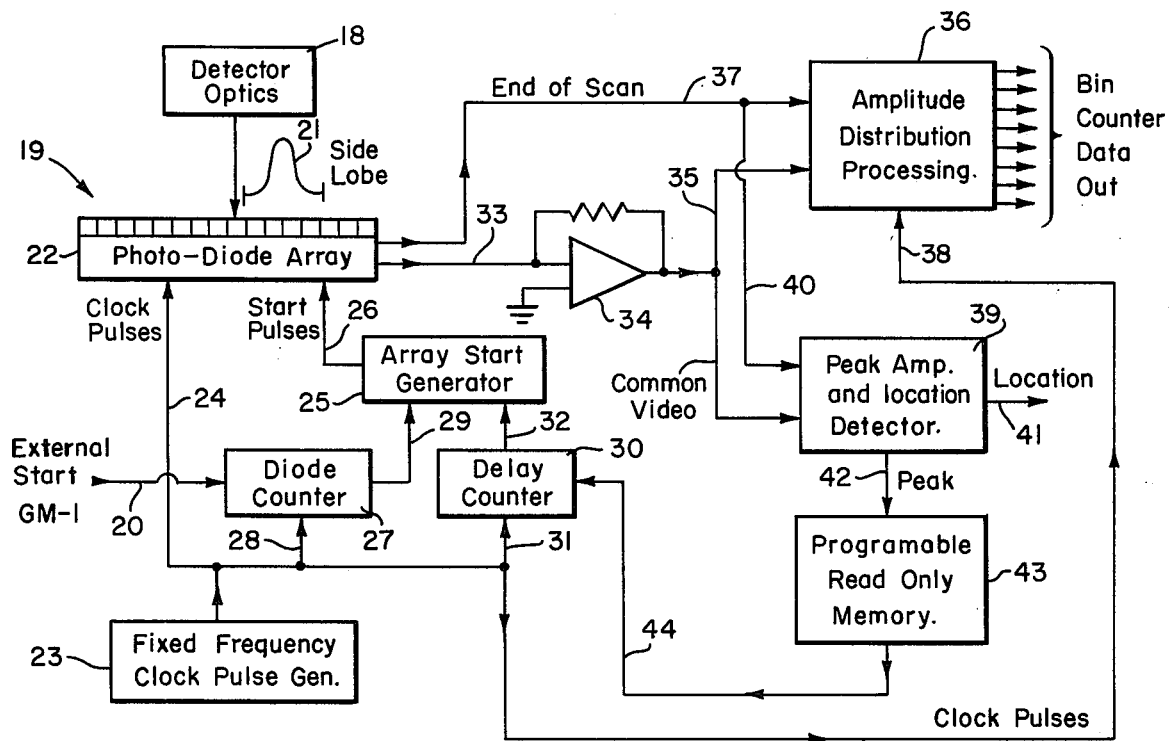
FIG. 2 is a block diagram of the basic analysis system incorporated in the processor of FIG. 1.

Referring now to FIG. 2, details of the processor 19 of FIG. 1 will be described. Referring to the upper left corner of FIG. 2, the detector optics block 18 is reproduced and this detector optics includes an optical squeezing means such as a cylindrical lens for directing and focusing a first order side lobe of a given diffraction pattern onto a linear photo diode array. The side lobe is schematically depicted at 21 in FIG. 2 and the linear photo diode array is shown at 22. This array may constitute one of the types provided by the Reticon Corporation heretofore referred to by the trademark RETICON.

At the lower left of FIG. 2, there is shown by the block 23 a source of fixed frequency clock pulses which connect through line 24 to the linear photo diode array 22 and function to carry out scanning by the array of the side lobe 21 from one side to the other.

Appropriate start pulses to start the scan of the photo diode array 22 are provided by an array start generator 25 connected to the photo diode array as by line 26. The external start signal from the scanning mirror GM-1 described in FIG. 1 applied on line 20 is received in a diode counter 27 the purpose for which will become clearer as the description proceeds. This diode counter is also supplied with clock pulses as indicated by the line 28 and has its output connected by line 29 to the array start generator 25.

Also connected to the array start generator 25 is a delay counter 30 provided by clock pulses from line 31 and arranged to control the start signal in the array start generator by connecting line 32. The purpose for this delay counter will also become clearer as the description proceeds.

When the linear photo diode array 22 scans the side lobe from one side to the other, there are developed a series of signals on an output line 33 which pass into an operational amplifier 34 to provide on a line 35 a series of voltage signals constituting a common video output. These voltage signals are passed into an amplitude distribution processing system depicted by block 36. In addition, an end of scan signal from the photo diode array is provided on line 37 and the fixed frequency clock pulses provided on line 38.

Shown below the amplitude distribution processing block 36 is a peak amplitude and location detector block 39 connected to receive the common video signal on line 35 and also the end of scan signal on line 37 by way of line 40. This block 39 will provide information as indicated at output 41 as to the location of the peak amplitude of the light lobe but more importantly serves to identify specifically the peak amplitude as on outlet line 42 for purposes of automatic exposure control.

This automatic exposure control includes a programmable read only memory circuit 43 connected through line 44 to the delay counter 30 heretofore referred to for delaying the generation of a start pulse for the linear photo diode array by an amount constituting a function of the peak amplitude detected by the block 39 all as will become clearer as the description proceeds.

Essentially, the amplitude distribution processing block 36 provides a plurality of counts indicated as bin counter data out in FIG. 2. These counts contain relevant information as to the shape of the light lobe 21 passed into the linear photo diode array 22.

In the successive analysis of successive diffraction patterns for the successive areas irradiated by the coherent beam across the fabric as described in FIG. 1, a succession of pluralities of counts will be provided from the block 36. Since the majority of the successive areas of the fabric inspected constitute good or fairly uniform fabric, these successive pluralities of counts will be equal or close to each other in value. A defective area in the fabric, on the other hand, will give rise to different count values for the plurality of counts characterizing the light lobe resulting from the defective area. Since the defects are relatively few over a large area of fabric, a histogram or history of successive pluralities of counts representative of "good" quality fabric can be accumulated and used for comparison with subsequently generated pluralities of counts such that a deviation from the stored count values serves to indicate a defect.

Figure 3:
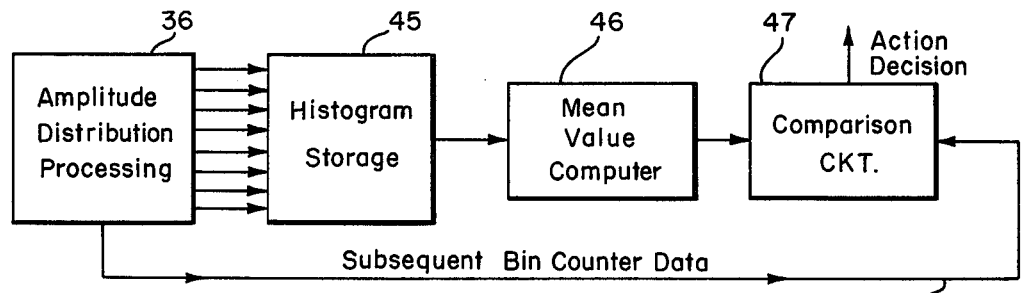
FIG. 3 is a further block diagram illustrating an important feature in the analysis in accord with the invention.

FIG. 3 shows in block diagram form the manner in which the foregoing can be carried out. Thus, the output data or plurality of counts from the block 36 are stored in a histogram storage block 45. From these stored pluralities of counts, a mean value for the counts is provided by a mean value computer 46. These mean values are then compared in a comparison circuit 47 with subsequent pluralities of counts as along line 48 provided from the block 36. A deviation by more than a given amount results in an action decision as indicated by the arrow from the comparison circuit 47. For example, such action decision would indicate that the specific area of the fabric under inspection deviates in quality from the normally processed "good" areas.

Grades can thus be assigned to the fabric under inspection.

All of the foregoing as well as further explanation of the operation of the block diagram of FIG. 2 will become clearer by now considering the remaining drawings.

Figure 4:
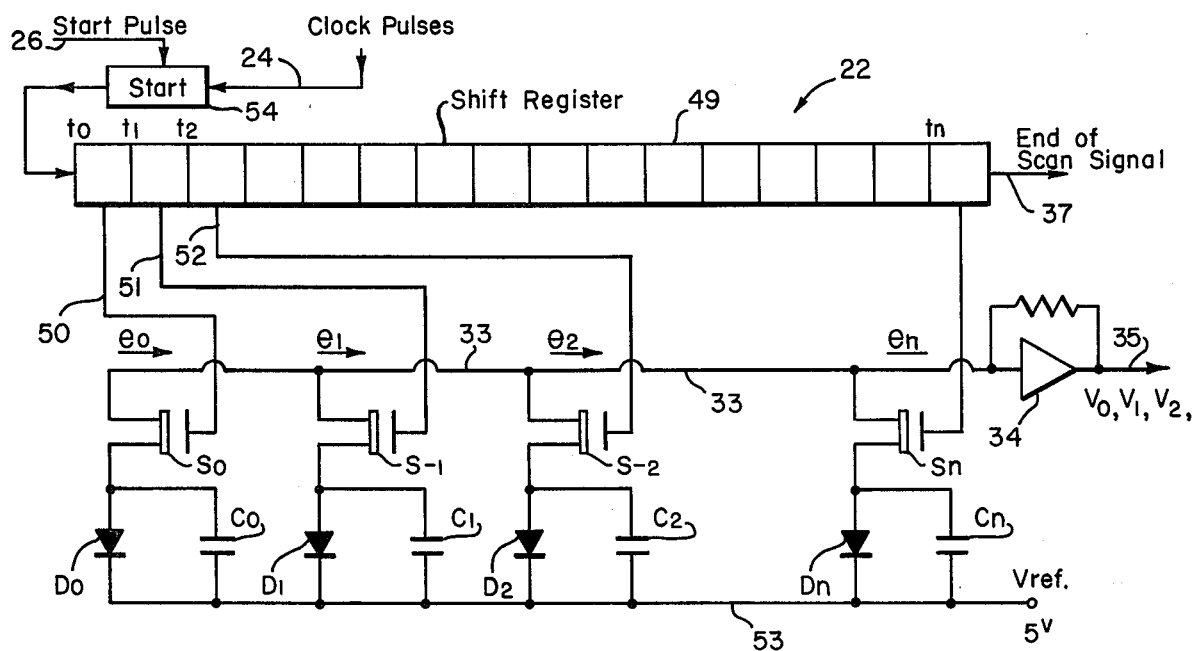
FIG. 4 is a simplified electrical diagram of a linear photo diode array and operational amplifier utilized in the system of the present invention.

Referring first to FIG. 4, there is shown the linear photo diode array 22 of FIG. 2 in greater detail. The light sensitive diodes are designated Do, D1, D2, and so forth to Dn. In a typical array used in the present invention, there might be provided a 128 such diodes making up the linear array. Each diode is shunted by a capacitor designated Co, C1 C2, and so forth to Cn. Each diode and its associated capacitor connect between the common video line 33 leading to the operational amplifier 34 through a metal oxide semi-conductor switch designated So, S1, S2 and so forth to Sn. Each switch, in turn, has its gate connected to the output of a shift register 49 as by lines 50, 51, 52 and so forth. The cathodes of the photo diodes together with one terminal of the capacitors all connect to a reference voltage line 53.

The various clock pulses on line 24 of FIG. 2 are shown entering the linear array at the top of FIG. 4 to pass through a start block 54 in turn triggered by the start pulse from the array start generator on line 26 of FIG. 2.

In operation, assume that the voltage on the upper terminal of the first capacitor Co is zero and that the switch So for the diode under discussion is open. The capacitor Co will be charged up to the Vref reference voltage on line 53. Light energy from the light lobe portion irradiating the diode Do creates an electric current which discharges the corresponding capacitor Co. Similarly, the remaining capacitors in this series, C1, C2 and so forth to Cn are discharged by light falling on the associated diodes, the amount of discharge being a function of the light intensity falling across the diode in its particular position in the array.

When now the start signal is applied to the array, the clock pulse will place a logic 1 in the first bit position of the shift register 49 causing the switch So to be closed through line 50 and resulting in the first diode being connected to the common video so that a first voltage signal is applied to the common video line 33. All other bits in the register 49 are zero so that the associated photo diodes are not connected to the common video. Successive clock pulses received in the shift register shift the single logic 1 down the register, sequentially connecting each photo diode to the common video line 33 so that successive voltage signals making up a series of voltage signals appear on this line, the values of which are respectively a function of the light intensity distribution of the light lobe from one side of the lobe to the other.

In the specific circuit described in FIG. 4, if it is assumed that the light intensity increases from one end of the array towards the center of the array and then decreases the voltage signals will have absolute magnitudes which progressively increase and then decrease. The voltage signals referred to are indicated in FIG. 4 at *eo, e1, e2* and so forth to *en*.

After these voltage signals pass through the operational amplifier 34 to the common video output line 35, they are inverted in polarity and result in a series of voltage signals which define an increasing and then decreasing overall signal encompassed within the time of one complete scan of the diodes by the shift register.

Figure 5:
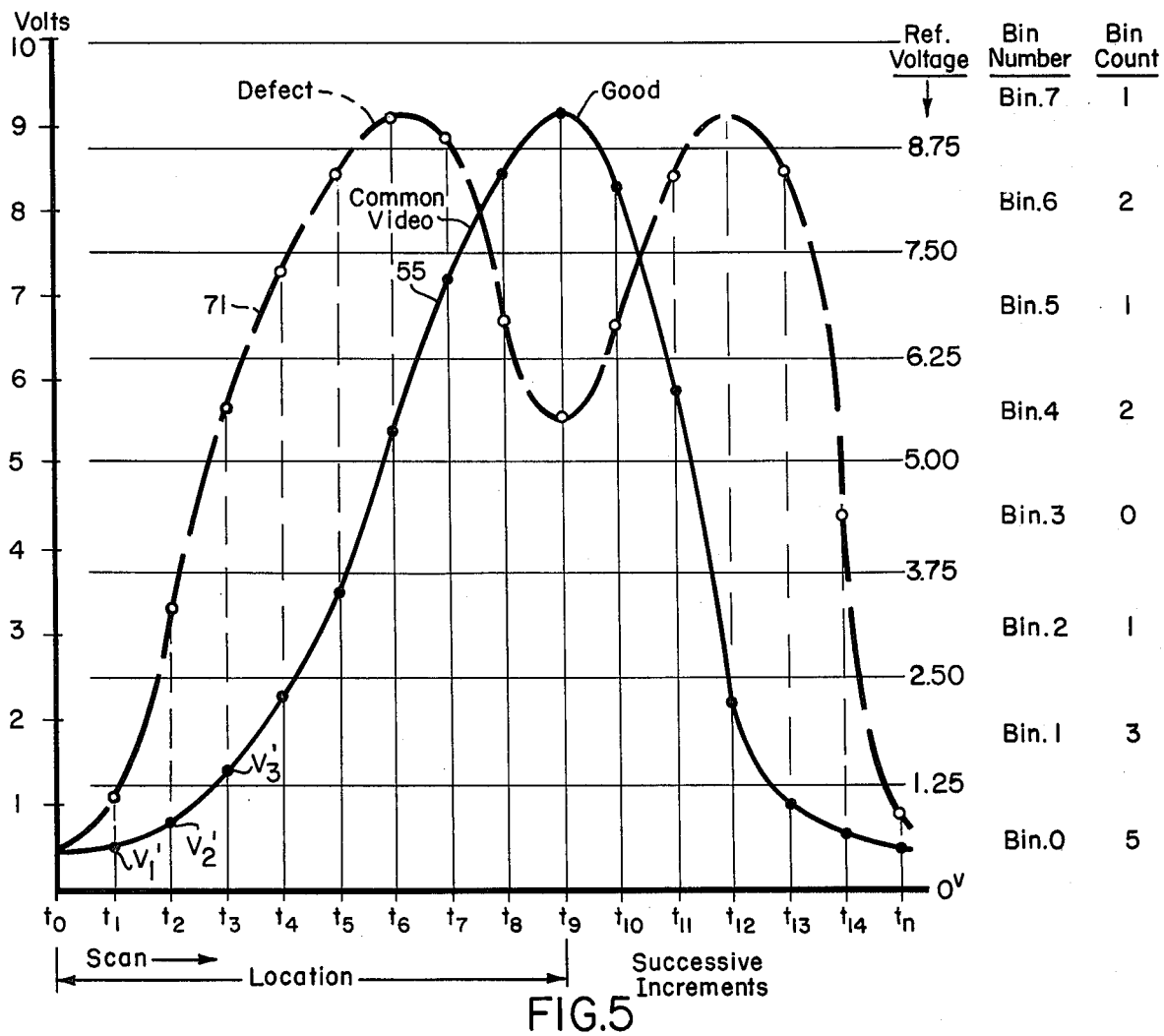
FIG. 5 are plots of the common video output signal from the operational amplifier of FIG. 4 resulting from the generation of successive voltage signals by the linear photo diode array.

Referring specifically to FIG. 5, this signal is indicated at 55 in solid lines and it will be seen that it constitutes the locus of various voltage points *v1, v2, v3*, and so forth constituting the series of voltage signals derived from the series of photo diodes in the array of FIG. 4.

The time of occurrence of the clock pulses are indicated along the abscissa of the plot of FIG. 5 as to, *t1, t2*, and so forth to *tn*. For a linear photo diode array comprised of 128 diodes, there will be provided 128 clock pulses required to complete one scan.

As wil be evident from FIG. 5, the clock pulses essentially define successively spaced increments from one side of the light lobe to the other during each increment of which there is provided a voltage signal whose respective voltage value is a function of the light intensity at that specific increment.

Figure 6:
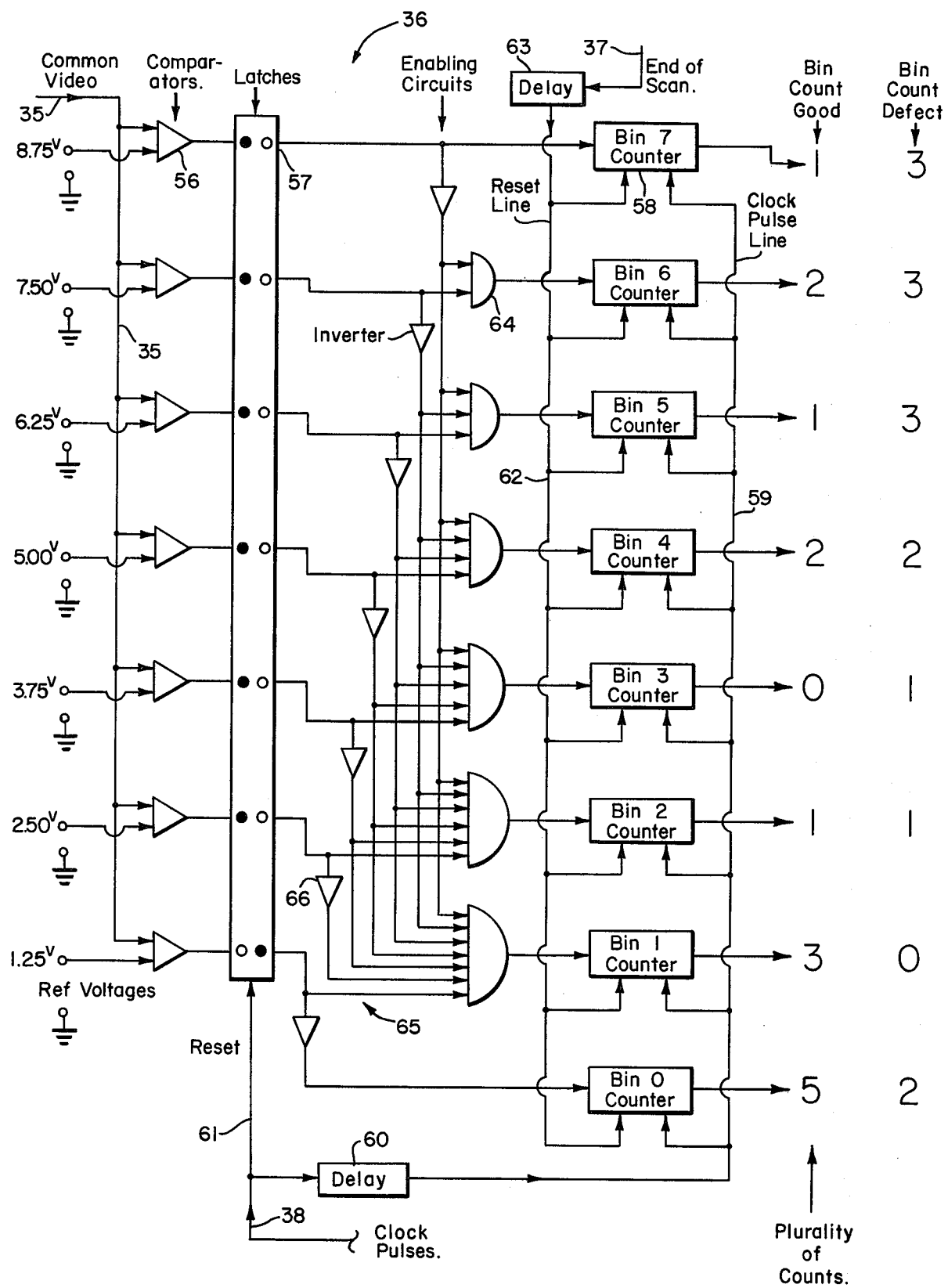
FIG. 6 is a more detailed electrical diagram partly in block form of the amplitude distribution processing block receiving the common video signal from the operational amplifier.

Referring now to FIG. 6, the series of voltage signals represented by the curve 55 of FIG. 5 appearing at the output line 35 of operational amplifier 34 from the linear photo diode array pass to the amplitude distribution processing block 36 shown in FIG. 2 and designated generally by this numeral in detail in FIG. 6. This block includes a series of individual comparators 56 having first inputs provided with successively increasing reference voltages and second inputs connected to the comon video line 35 to receive the series of voltage signals. The outputs of the comparators 56 connect in turn respectively to a series of latches 57. The voltage signals successively provided from the linear photo diode array are thus each compared by each comparator with its associated reference voltage. Each comparator in turn will set its connected latch only if its received voltage signal exceeds its reference voltage.

Shown to the right of FIG. 6 is a series of counters 58 each connected to the source of fixed frequency clock pulses as by line 59 connecting from the output of a delay circuit 60 in turn receiving the clock pulses on line 38 described in FIG. 2. The same clock pulses on line 38 pass directly through line 61 to serve as latch resetting signals to the latch means 57.

The series of counters 58 also receive reset signals from a common line 62 connected from a delay circuit 63 in turn receiving the end of scan pulse on line 37 described in FIG. 2. The counters are thus reset at the end of each scan of the linear photo diode array whereas the latch means 57 are reset at each clock pulse.

In the central portion of FIG. 6, there is shown a series of enabling circuits 64 interconnected between the latches and counters as by various leads designated generally by the numeral 65. The arrangement is such that the enabling circuit means enables only that counter connected to a set latch associated with the comparator with the highest reference voltage, so that counts are accumulated in the enabled counters over the scan period. The total counts in each counter provides a plurality of counts indicative of the shape of the amplitude envelope of the light lobe as described at the output of the block 36 in FIG. 2.

The manner in which the foregoing is accomplished will be better understood by considering the specific example of the voltage signals defined by the curve 55 of FIG. 5. In this respect, the various reference voltages for the comparators 56 have been reproduced along the right hand side of the plot of FIG. 5 in proper positions to indicate voltage values for the ordinate axis of the plot. These fixed reference voltages define horizontal equally spaced lines in the diagram to divide the wave form 55 into what is referred to as "bins".

More particularly, for voltages between the value zero volts and the first reference voltage 1.25, there is designated the bin 0. The voltages between the reference voltages 1.25 and 2.50 comprise the bin 1, and so forth for bin 2, bin 3, bin 4, bin 5, bin 6 and finally bin 7. In the example set forth, the reference voltages progressively increase in steps of 1.25 volts.

At this point it is to be noted that the number of bins is substantially less than the number of photo diodes in the array and thus substantially less than the incremental spacing at which voltage signals are generated. As will become clearer as the description proceeds, this lesser number of bins greatly reduces the relevant data characterizing the light lobe amplitude envelope to the end that data storage requirements are substantially reduced and high speed operation in processing results.

Considering FIGS. 5 and 6 together, at the beginning of the scan at times *t*1 and *t*2, the voltage signals *v*1 and *v*2 will be received in all of the comparators 56 of FIG. 6. However, since the voltage signals *v*1 and *v*2 are both less than the reference voltage 1.25 volts, they fall in bin 0 and the latch associated with the comparator having a reference voltage of 1.25 volts will not be set. Moreover, none of the other latches associated with the other comparators will be set since their reference voltages are all higher than either of the voltage signals *v*1 and *v*2. As a result, none of the counters will be enabled with the exception of the bin 0 counter. Bin 0 counter is enabled because of the provision of inverter 66 in the input line from the latch to this counter which provides an enabling signal from the input voltage signals to the comparator only so long as the associated latch is not set.

Bin 7 counter at the top of FIG. 6 is not energized since the signal from the associated latch means is not a result of a setting of this latch and there is no inverter in the line to the bin 7 counter. Bin 6 counter is not energized or enabled since there is no setting of its associated latch to provide an input signal to the coincidence circuit 64 for providing an output signal even though the other input to the coincidence or enabling circuit is provided as a result of the inverter from the top line.

Similarly, the remaining counters except for the bin 0 counter are not energized as described since the associated enabling circuits in the form of coincidence circuits 64 do not all have an input simultaneously on their input lines.

Referring back to FIG. 5, consider now the time increment $t3$ wherein the voltage signal $v3$ exists and is compared simultaneously in all of the comparators 56 of FIG. 6. In this case, voltage $v3$ falls within the reference voltage interval 1.25 volts and 2.50 volts; that is, bin 1. Since this voltage signal exceeds the reference voltage 1.25 volts, the latch associated with the lower comparator wll be set, the setting of this latch being indicated by the black circle to the right of a white circle. Since the signal $v3$ is less than the remaining reference voltages, none of the other latches is set as indicated by the black circle to the left of the white circles in each of the latches.

The setting of the latch associated with the comparator with reference voltage 1.25 volts results in a signal which is inverted by the inverter 66 to this disable the bin 0 counter. However, this signal prior to inversion by the inverter 66 passes directly into a first input of the coincidence circuit associated with the bin 1 counter.

It will be noted that the six other inputs to the coincidence circuit associated with bin 1 counter also are provided with signals from the various input lines each of which constitutes the output of an inverter associated with the latch signal line for the remaining latches. Thus all of the inputs to this concidence circuit are energized simultaneously and an output signal therefrom energizes bin 1 counter which will count the $v3$ voltage signal.

In a similar manner, for each successive time increment one and only one counter will be enabled when the voltage signal falls within adjacent reference voltages defining the bin associated with that counter and disabled or terminated whenever the received voltage signal has a value falling outside the bin or voltage interval between the reference voltage of the comparator and the adjacent comparator having a higher reference voltage.

Figure 7:
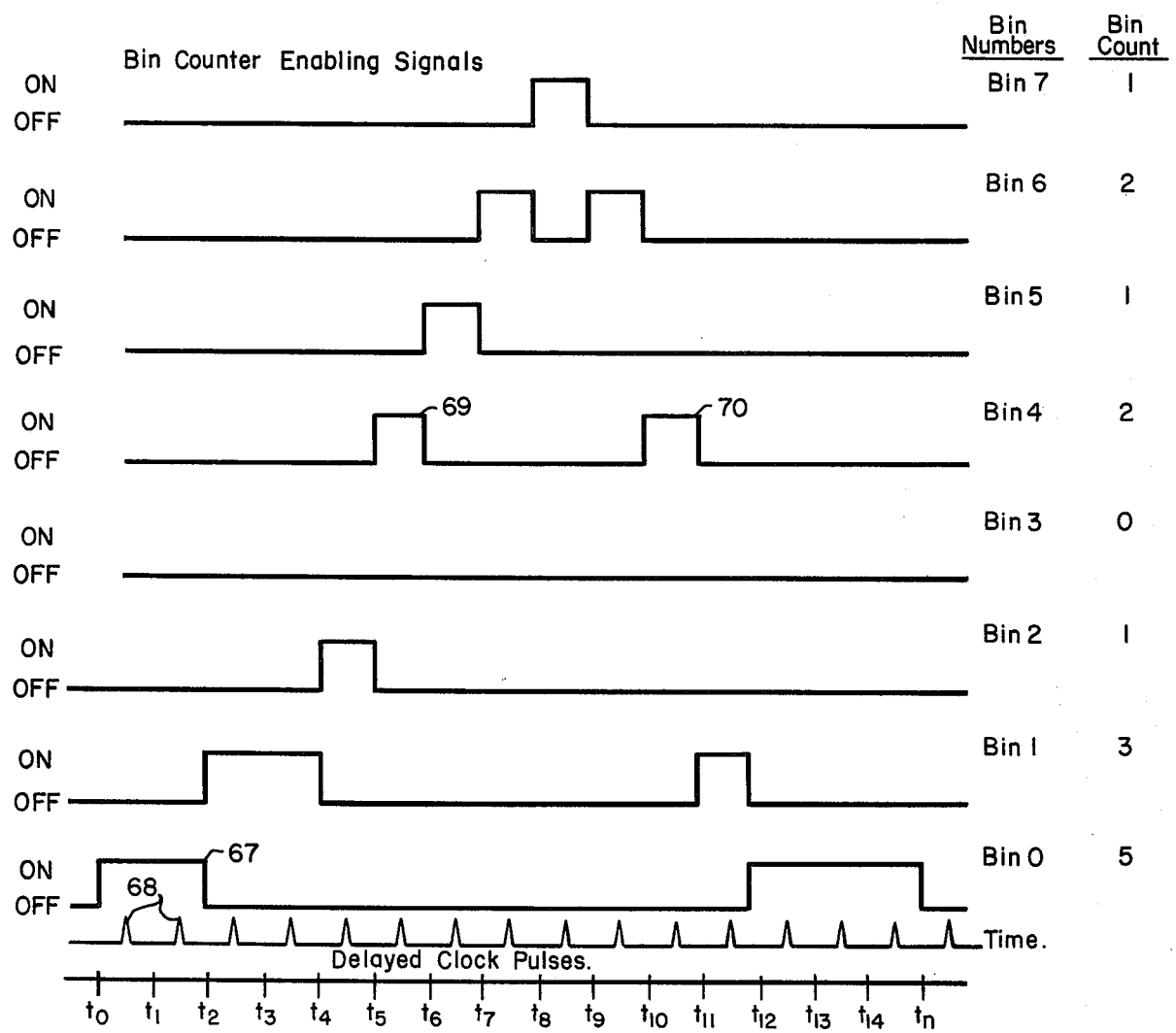
FIG. 7 is a diagramatic representation along a time axis indicating points in time that enabling signals are provided to various components in FIG. 6.

The output signals from the various coincidence circuits making up the enabling circuit 64 in FIG. 6 are depicted for the particular voltage signal wave form 55 of FIG. 5 in FIG. 7. The FIG. 6 bin 0 counter is enabled during the time intervals indicated by the FIG. 7 square wave envelope 67 which encompasses clock pulses 68, these clock pulses being delayed slightly by the delay circuit 60 described in FIG. 6 prior to passing to the various counters so that they will fall within the square wave envelope 67. Disabling of the bin 0 counter is indicated at time $t2$ and simultaneously the bin 1 counter is enabled as indicated by the next wave form.

Considering the counter associated with bin 4, it will be noted that it is enabled twice during the overall scan period as at 69 and 70 i.e., in FIG. 7 during the time periods $t5$-$t6$ and $t10$-$t11$. This enabling permits counting of the delayed clock pulses initially occurring at the times $t5$ and $t10$. In FIG. 5 these specific points constitute two points wherein the curve 55 is in bin 4. The bin counts by all of the counters are indicated in both FIGS. 5 and 7 as well as in FIG. 6.

Essentially, it will be clear that for each scan, there are provided a plurality of counts by the bin counters which characterize the intensity distribution of the light lobe over the linear photo diode array.

In the example of the solid line voltage signal curve 55 of FIG. 5, the exemplary bin counts constitute a plurality of counts characterizing a "good" light lobe or diffraction pattern. In subsequent analysis of successive light lobes, a defect in the fabric could result in voltage signals following a curve indicated by the dashed lines 71 in FIG. 5. This curve is marked defect as opposed to the "good" solid line curve 55.

The corresponding voltage signals from the linear photo diode array are depicted by the points of interception of this curve with the vertical incremental time lines $t1$, $t2$, $t3$, etc. and it will be noted that these points are different in number for each of the bins under consideration. Thus, there is provided a plurality of counts in the counter which characterize a defect. In the specific example, the bin count for the dashed curve 71 is illustrated in FIG. 6 to the right of the bin counts for the "good" sample.

It will be noted that in general there are a greater number of bin counts in the higher numbered bins for a defect diffraction pattern as compared to a "good" diffraction pattern. Another distinction is that in general there will be a considerably greater number of counts in the lower numbered bins for a "good" diffraction pattern compared to a defect diffraction pattern.

It will now be evident that the output bin count from the processing block 36 provides data characterizing the amplitude distribution or amplitude envelope of the light lobe and further it will be evident that should this bin count or plurality of counts in the various counters deviate from those counts characteristic of a good fabric, there will be provided an indication that a defect is present.

The significance of the block diagram of FIG. 3 in this invention can now be appreciated. Since as a practical matter and as stated heretofore, defects constitute only a small percentage of the entire area of fabric investigated, it is possible to form a histogram of good samples, compute the mean value of the plurality of output counts characterizing the good samples and use these for comparison with subsequent pluralities of counts to detect any defects. By utilizing previously stored good examples of bin counts the mean values of which have been computed over a succession of such counts, a relative comparison is made for any one bolt of fabric material and variations in density, for example, from bolt to bolt of fabric will not affect the outcome.

Thus, again referring to FIG. 3, the bin counter output data or plurality of counts for each sampling is stored in the histogram storage block 45 and the mean value of each of the counts making up the successive plurality of counts for good fabric computed in the mean value computer 46. These values as described heretofore are then compared in comparison circuit 47 with subsequent bin counter data from line 48 and if there is a deviation above a certain amount, an action decision signal will be provided indicating a defect is present.

With reference once again to FIG. 1, in the preferred embodiment of this invention, the histogram of a succession of pluralities of counts from the bin counters is stored for each light channel 15 individually; that is, successive areas of the fabric exposed in a vertical sense as a result of the moving fabric are stored so that the histogram in block 45 of FIG. 3 constitutes sammples taken along one light channel for comparison with subsequent samples along the same light channel. By comparing the histograms with subsequent diffraction patterns in this manner, any slight characteristic differences in the light channels are eliminated from affecting the results.

Figure 8:
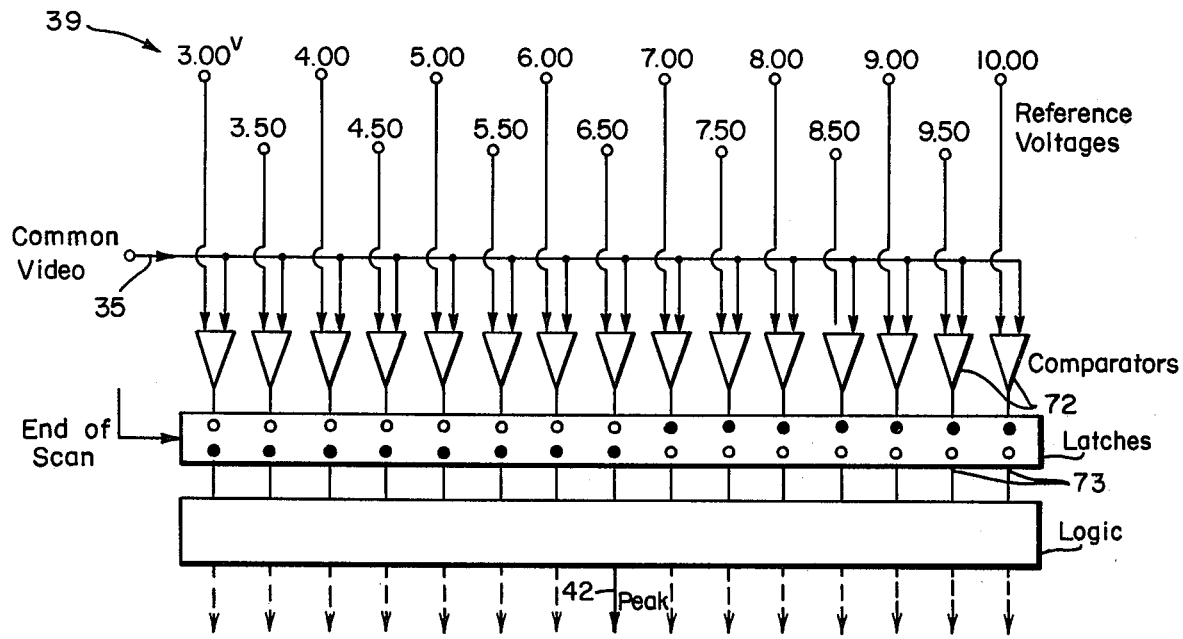
FIG. 8 is an electrical diagram partly in block form of the peak amplifier and location detector of FIG. 2.
Figure 9:
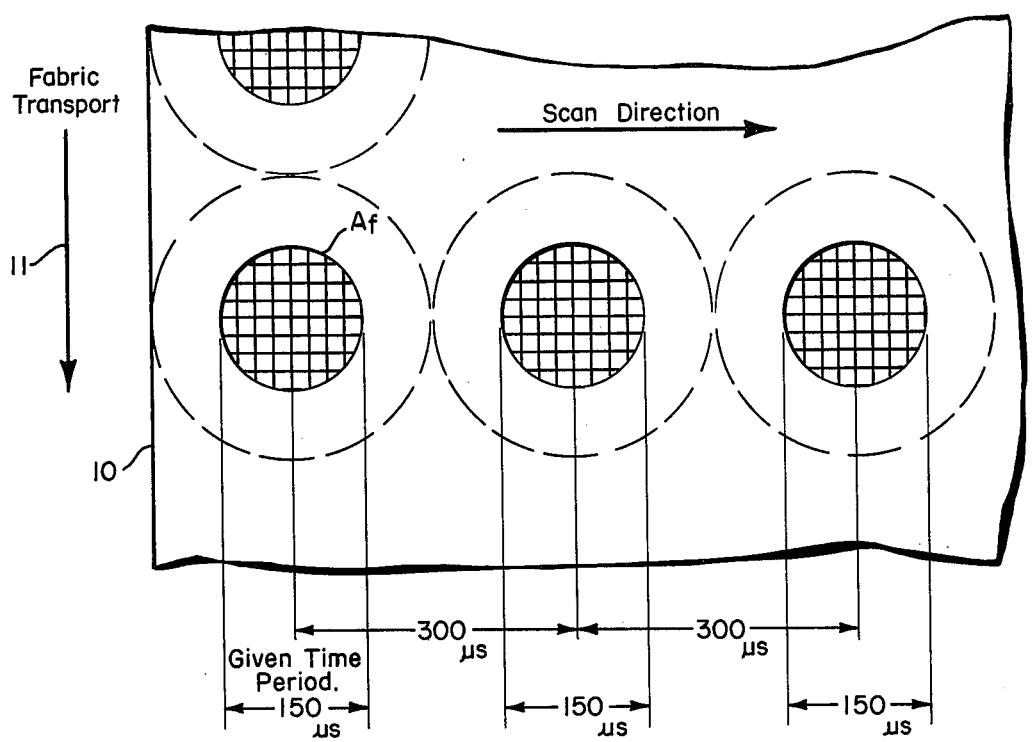
FIG. 9 is a fragmentary front elevational view of a portion of fabric material analyzed by the system of the present invention useful in explaining the overall operation of the preferred embodiment; and, FIG. 10 illustrates an automatic exposure control arrangement utilized in the analysis in accord with this invention.
Figure 10:
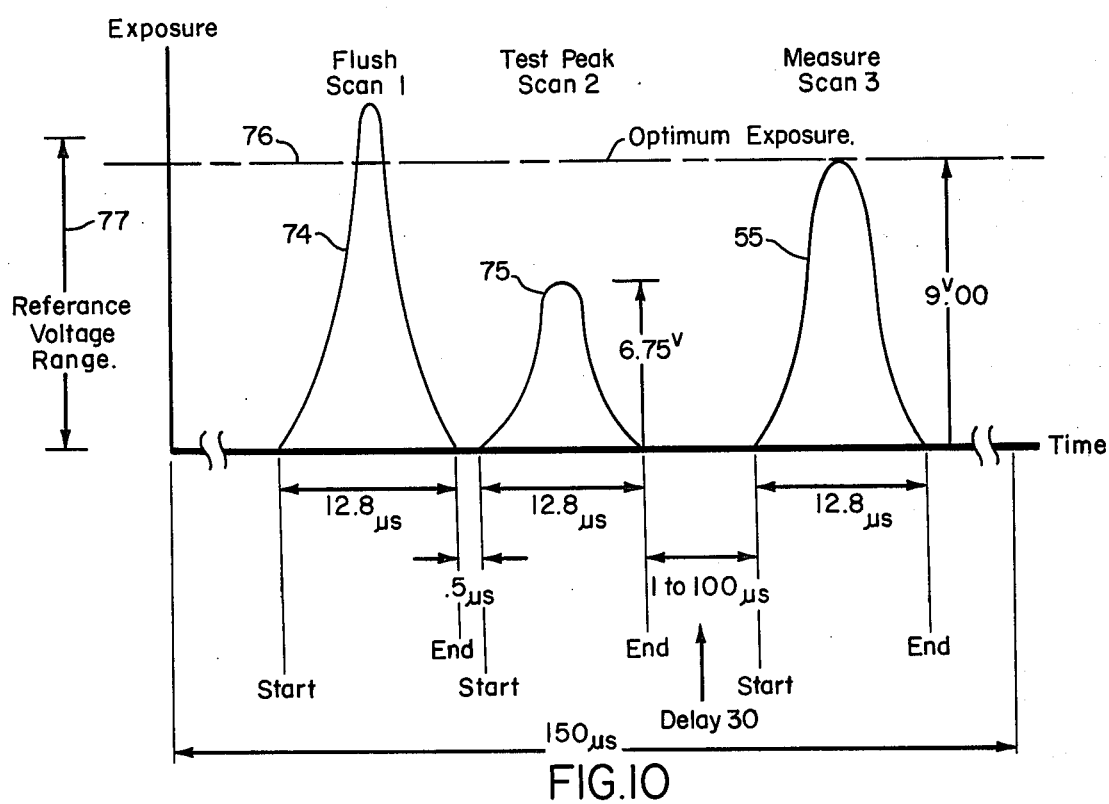

Referring now to FIGS. 8, 9 and 10 in conjunction with the block diagram of FIG. 2, further features of this invention will be described.

FIG. 8 shows in detail one example of a peak amplitude and location detector useful in conjunction with an automatic exposure control briefly referred to heretofore in FIG. 2. It will be recalled that the varying light intensity of the light lobe falling on the linear array of photo diodes results in the generation of voltage signals by sampling the voltage on each of the capacitors which voltage is determined by the amount the capacitor has been discharged by its associated photo diode. In the event the amount of light in the light lobe is relatively weak, the voltage signals on the common video output from the linear array will correspondingly be of small absolute magnitude and thus may never rise above some of the lower given reference voltages for the comparators of FIG. 6. On the other hand, if an extremely bright light lobe is analyzed, too much light will be present resulting in the bin counters associated with the higher reference voltages only being activated.

In view of the foregoing, it is important that the light falling on the linear array be such as to provide voltage signals which cover the span of the given range of reference voltages in the comparators; that is, the light should be such as to provide voltage signals which essentially "fill" the given range. In this manner, optimum output data will be provided and the "shape" of the light lobe can be accurately depicted regardless of the absolute intensity of the overall lobe; that is, independently of the overall intensity.

It will further be recalled that the absolute value of the voltage signal is determined by the length of time that a diode in the linear array is exposed to the available light in the particular spatial or time increment at which a particular voltage signal is supplied to the common video line. If the time of exposure of a particular diode is increased, there will be a greater discharge of its associated capacitor prior to sampling to provide a given voltage signal whereas if this exposure time is decreased, there will be less discharge of the capacitor at the time of sampling. By thus controlling the length of time of exposure of all of the diodes to the light lobe, a control of the absolute magnitudes of the voltage signals can be realized to provide the desired proper filling of the reference voltage range.

In order to control the exposure time, it is necessary first to determine the peak amplitude or intensity in the light lobe from one side of the lobe to the other. This peak intensity will provide an indication of the highest of the series of voltage signals generated by the diode array and this value can then be utilized to adjust the overall exposure time. For example, if the highest peak intensity measured is relatively small; for example, about one half of the highest reference voltage, an adjustment can be made to increase the exposure of all of the diodes to the light lobe prior to actual genneration of the voltage signals to bring up the voltage signal associated with the highest peak to a value corresponding to the highest reference voltage in the reference voltage range.

In the effecting of the automatic exposure control, it is therefore necessary to detect the highest intensity voltage signal among the various voltage signals to be analyzed and it is for this purpose that the circuit of FIG. 8 is used. Essentially, this circuit operates similarly to the comparators, latch means and enabling or logic circuits described in FIG. 6 in that the voltage signals are compared with a range of reference voltages in a plurality of comparators. However, counters are not necessary in the peak detector of FIG. 8, but rather only the provision of a signal indicative of the highest peak. Thus, the comparators are shown at 72, there being provided fifteen as opposed to seven shown in FIG. 6, each provided with progressively increasing reference voltages in steps of one half volt by way of example. The voltage signals on the common video line 35 pass into the second inputs of the comparators as shown. The output of each comparator connects to an associated latch means 73, the outputs of the latch means in turn connecting to a logic block. This logic block includes a plurality of coincidence circuits similar to the circuits 64 of FIG. 6.

Rather than a resetting of the latch means 73 at each increment of time; that is, at each clock pulse, the latches are not reset until the end of each scan period of the diode array. The end of scan signal on line 40 is shown connected to the latches to reset the same.

Referring now back to FIG. 2, the external start pulse on line 20 synchronized to the scanning mirror GM-1 is received in the diode counter 27. This diode counter will count exactly 128 clock pulses from the fixed frequency clock pulse generator 23 which corresponds to a period of time exactly equal to one scan of the photo diode array. During this scan period, the diodes are all exposed for the entire scan period to the light side lobe 21 and thus are all "flushed" or cleared of any voltage signals. In other words, the capacitors associated with each diode are wholly discharged. An end of scan signal is generated at the end of this first scanning period determined by the diode counter 27 which resets the latch means of both FIGS. 6 and 8 and also the counters. A start scan pulse is then immediately generated and the array is scanned by the clock pulses as described heretofore. Since the diodes are exposed to the side lobe only for the length of time between the end of scan signal and the start signal for this second scan, there will only be small voltages on the capacitors comprising the series of voltage signals. However, the values of these voltage signals will be different from each other depending upon the intensity changes in the side lobe from one side to the other. These voltage signals from this second scan pass to the comparators of FIG. 8 and a latch is set for that comparator having a reference voltage closest to the highest voltage value of the series of voltage signals. In the example shown in FIG. 8, the latch associated with the comparator having a reference voltage of 6.5 volts is set along with all latches associated with comparators having reference voltages less than 6.5 volts. This corresponds to a peak voltage over the light lobe as detected during the second scan of between 6.5 and 7.0 volts and this signal only is selected by the logic block and passed on line 42 to the block 43 of FIG. 2.

This signal selects a predetermined one of the internal memories in block 43 which is thereby automatically read out as an appropriate signal to control the amount of delay effected by counter 30 between the end of scan pulse after the completion of the second scan and the next start pulse. This delay time permits sufficient exposure of the diodes before the start of a third scan to provide resulting voltage signals which fill the range of the reference voltages. The length of this exposure period is thus inversely proportional to the value of the peak signal detected during the second scan.

When the third scan starts, the generated voltage signals are then processed by the block 36 constituting the circuit of FIG. 6 to provide a bin count or plurality of counts in the counters characterizing the amplitude envelope of the light lobe.

The entire above described process is repeated after the end of scan signal from each third scan so that in the sampling of any one specific light lobe, three scans occur. First, a flushing scan period controlled by the diode counter 27, second, a test peak scan started with only minimum exposure of the diodes to determine the maximum or highest intensity amplitude in the light lobe, and third, after an adjustment of the exposure time for starting of the next scan, a normal scanning of the array to provide the voltage signals actually counted by the counters of FIG. 6 to provide the desired bin count data.

The foregoing operation will be better understood by now referring to FIGS. 9 and 10.

Considering first FIG. 9, there is illustrated a typical scanning situation for the fabric 10. It is assumed in this example that the overall width of the fabric from one edge to the other to be scanned is four feet and that each successive area of scan Af has a diameter of about one inch and that there are a total of 20 successive areas across the width of the fabric. If the fabric is moving in the vertical direction of the arrow 11 at a speed of 120 yards per minute and the next row of scans across the fabric is to assume a proper position above the first scan in order to cover the entire fabric area, the period between the time that one successive area is irradiated to the next successive area is about 300 microseconds. In FIG. 9 it will be understood that the scanning arrangement is similar to that described in the heretofore referred to copending application entitled COHERENT SCANNING SYSTEM FOR FABRIC INSPECTION. Thus, it will be understood that one side of the fabric is scanned from left to right and then a switched laser beam scans the opposite side to fill in the gaps between the successive areas on the one side. With such an arrangement, there will be provided, as noted, the 300 microsecond time interval between successive areas.

The time that a given area is actually irradiated by the coherent light during the scanning by the scanning mirror is made equal to about 150 microseconds, such being acccomplished by providing a light beam of greater diameter than the diameter of the area Af, this greater diameter being depicted by the dashed circles.

From the foregoing, it will be evident that the three scans described heretofore must all take place within this given time period of 150 microseconds for each successive area. Also, the variable time allotted for the automatic exposure control must be encompassed within this 150 microseconds.

With the comparator and latch circuitry described, it is easily possible to encompass the three described scans for each successively exposed area well within the 150 microsecond period.

FIG. 10 illustrates the foregoing wherein the first scan or flushing exposure time over a scan period of the diode array is accomplished in 12.8 microseconds; that is, the diode counter for 128 diodes will count 128 clock pulses in a period of 12.8 microseconds.

This flush scan is designated 74 in FIG. 10. As described, immediately after this first flush scan, the scan 2 is started with the diodes exposed a minimum length of time so that the peak intensity can readily be detected. In the example described wherein during the test peak scan 2 the peak intensity was in the area of 6½ volts; that is, in the reference voltage interval between the comparator in FIG. 8 having a reference voltage of 6.5 volts and the adjacent comparator having a reference voltage of 7 volts. The test peak is shown at 75. This highest peak voltage signal resulted for a minimum exposure time in the example shown in FIG. 10 of 0.5 microseconds.

This value of 6.5 reference volts which is exceeded by the test peak results in the latch associated with the comparator receiving 6.5 volts being set as described in FIG. 8 to provide an appropriate signal to the program read only memory block 43 in FIG. 2 which transforms this signal into a function to control the delay counter 30 such that the next scan pulse for the measure scan 3 in FIG. 10 will not start until a sufficient exposure to the diodes has elapsed to assure that the highest or maximum intensity voltage signal will fill the reference voltage range.

Thus, the actual scan for measurement purposes is indicated at 55 in FIG. 10 wherein the same has been delayed in its start for a period which may vary between 1 and 100 microseconds by way of example. The voltage reference range filled by this maximum voltage signal is indicated to the left of FIG. 10 at 77.

It is this third or last scan in the series shown in FIG. 10 which will then energize the enabling circuits and counters to provide a bin count data output constituting a plurality of counts utilized in depicting the shape of the light lobe.

Because of the automatic exposure control, it will be evident that the output data is really independent of the absolute magnitude of the highest intensity amplitude in the light lobe, all as described heretofore.

From an inspection of FIG. 10 even if the delay after the test peak scan 2 and the start of the measure scan 3 is 100 microseconds, or even slightly greater, there is still ample time for the three scans to take place within the overall 150 microsecond period, each of the scans for the 128 diodes described being only 12.8 microseconds.

Finally, in conjunction with the test peak scan 2 measurement of the intensity of the highest intensity amplitude in the light lobe, information is simultaneously provided for determining the location of this maximum amplitude signal. Thus again referring to FIG. 8, the particular comparator circuit and associated latch which is set by the maximum voltage signal during the test scan can readily be correlated to the time increments of the scan shown in FIG. 5. For example, the maximum peak for the good voltage signal curve 55 occurs at the time $t9$ and this can be correlated with the beginning of the scan to thereby provide an indication of the location.

It will be understood in the various drawings that the abscissa time increments shown as $t0$, $t1$, $t2$ and so forth actually total 128 in number for a linear diode array comprised of 128 diodes. Only fourteen or fifteen such increments have actually been illustrated in the figures for purposes of clarity.

However, the number of bins for providing the output plurality of counts may in actual practice be a total of eight such bins as shown and described so that in effect, there will be a plurality of eight separate counts in the respective counters which data characterizes the shape of the light lobe amplitude envelope. This vastly reduced amount of data as a consequence of the bin arrangement avoids the necessity of processing separately all 128 voltage signals provided from the diode array.

Moreover, and as stated heretofore, the provision of the comparators and latches as described completely eliminates the need for any peak sensing and holding type analog circuits as utilized in prior art detectors and enables the extremely rapid processing described within the available period of time as set forth in FIG. 10.

A particularly important consequence of the particular circuits employed is the fact that the actual position of the squeezed light lobe along the diode array is not critical since the bin count will be the same whether the lobe is closer to one side of the array or the other. For example and with reference to FIG. 5, if the curve 55 is shifted bodily horizontally along the scan axis, the bin counts will remain the same. This feature thus avoids the necessity of critical placement of the array relative to the light lobe or critical directing of the light lobe on to the array in the horizontal direction.

It should be understood that by scanning of the light lobe from one side to the other is meant that a cross section of the lobe is scanned.

From the foregoing description, it will thus be evident that the present invention has provided a greatly improved method and system for the analysis of a light lobe and particularly the analysis of first order side lobes in successive diffraction patterns developed in a moving fabric inspection system.

What is claimed is:

1. A method of analyzing the shape of the amplitude envelope of a light lobe including the steps of:
  a. scanning the light intensity of the lobe from one side of the lobe to the other to provide successive voltage signals whose respective voltage values are a function of the light intensity at successively spaced increments from the one side to the other;
  b. providing a series of reference voltages of substantially less number than the number of spaced increments, each reference voltage having a value greater than the value of the preceding reference voltage in the series to define a voltage range encompassing the highest voltage in said series of voltage signals;
  c. comparing each successive voltage signal with all of said reference voltages simultaneously; and
  d. providing a numerical count of those voltage signals which have voltage values falling between the values of adjacent reference voltages in said series of reference voltages so that a plurality of counts is provided which indicates the amplitude distribution of light in said light lobe, said plurality of counts being substantially less in number than the number of spaced increments thereby reducing storage data requirements in the analysis of the amplitude envelope of said light lobe.

2. The method of claim 1, including the steps of analyzing a series of successive light lobes, each in accordance with the first mentioned four steps, to provide successive pluralities of counts; computing the mean values of the counts from a succession of said pluralities; and referencing subsequent pluralities of counts to said mean values whereby deviations by a given amount of one of said subsequent pluralities of counts from said mean values indicates a change in the amplitude envelope of that successive light lobe characterized by said one of said subsequent pluralities of counts.

3. The method of claim 1, in which said light lobe constitutes a first order side lobe in a diffraction pattern resulting from passing coherent light through a material to be inspected and in which said method includes the steps of successively passing the light beam through different areas of the material to cover a large area and thereby develop successive side lobes, each successive side lobe being scanned and analyzed in accordance with the first mentioned four steps to provide successive pluralities of counts; computing the mean values of the counts from a succession of said pluralities; and referencing subsequent pluralities of counts to said mean values whereby defects in said material which occur infrequently can be readily detected when a subsequent plurality of counts deviates from said mean values by a given amount.

4. The method of claim 1, including the step of correlating the position of that spaced increment during which the voltage signal having the highest voltage value is provided with the beginning of said successively spaced increments to thereby provide an indication of the location of the peak amplitude of said light lobe.

5. The method of claim 1, in which said scanning of the light intensity of the lobe from one side to the other includes the steps of exposing a series of photo diodes at said successively spaced increments to said light lobe for a given time period; and then test scanning said diodes successively to provide successive voltage signals, said method including the further steps of adjusting a time period of exposure in accordance with the value of the peak voltage signal to vary the level of the voltage signals in a subsequent measurement scanning of the diodes in such a manner as to substantially fill said voltage range defined by said reference voltages.

6. The method of claim 1, in which said plurality of counts are provided within one hundred and fifty microseconds of the point in time that said scanning of the light intensity of said lobe starts.

7. A system for analyzing the shape of the amplitude envelope of a light lobe including, in combination:
  a. photo-detector means for scanning said lobe from one side to the other to provide a series of voltage signals whose voltage values are functions of the light intensity at successively spaced increments from the one side of the lobe to the other;
  b. comparator means receiving said voltage signals and having given reference voltages increasing in a series of steps to cover a given range for comparison with said voltage signals; and;
  c. counter means responsive to said comparator means to provide a numerical count of those voltage signals which have voltage values falling between the values of adjacent reference voltages in said series of steps whereby a plurality of counts is provided which indicates the amplitude distribution of light in said light lobe.

8. A system according to claim 7, in which a series of successive light lobes are time sequentially analyzed to provide successive pluralities of counts, said system further including storage means connected to said counter means to store said successive pluralities of counts; computing means connected to said storage means for computing the mean values of counts from a succession of said pluralities stored therein; and comparison circuit means receiving said mean values and comparing the same with subsequently generated pluralities of counts and responsive to deviations of one of said subsequently generated pluralities of counts from said mean value by a given amount to provide information indicating a change in the amplitude envelope of that successive light lobe characterized by said one of said subsequently generated pluralities of counts.

9. A system according to claim 7, in which said comparator means includes a series of individual comparators and a series of latches connected to the outputs of the comparators respectively and in which said counter means includes a series of counters, a source of clock pulses connected to the counters, and enabling circuit means interconnecting said counters with said latches, each of said comparators setting its connected latch only if its received voltage signal exceeds its reference signal, said enabling circuit means functioning to enable only that counter connected to the set latch associated with the comparator with the highest reference voltage and terminate operation of said counter when the received voltage signal has a value falling outside the voltage interval between the reference voltage of said comparator and the adjacent comparator having a higher reference voltage in said series of steps.

10. A system for analyzing the shape of the amplitude envelope of a light lobe within a given period of time including, in combination:
   a. a photo-detector linear array positioned to receive the light information generated by said lobe;
   b. a source of fixed frequency clock pulses connected to said array;
   c. an array start generator for providing a start scan pulse to said array at a point in time within said given period of time to apply said clock pulses to the array so that the photo diodes in the array are successively actuated from one end to the other by the clock pulses to define one scan of the array, said array having a common video output upon which successive voltage signals representative of the amplitude envelope of the light intensity of said lobe are provided;
   d. a series of comparators provided with successively increasing reference voltages connected to receive said successive voltage signals;
   e. a series of latches respectively connected to the outputs of the comparators, the voltage signals successively provided from said array each being compared by each comparator with its associated reference voltage, each comparator setting its connected latch only if its received voltage signal exceeds its reference voltage;
   g. a series of counters connected to said source of fixed frequency clock pulses; and
   h. a series o enabling circuits interconnected between the latches and counters to enable only that counter connected to the set latch associated with the comparator with the highest reference voltage, whereby counts are accumulated in the enabled counters over said one scan, the total counts in each counter providing a plurality of counts indicative of said shape of the amplitude envelope of said light lobe.

11. A system according to claim 10, in which said light lobe constitutes a first order side lobe in a diffraction pattern resulting from passing coherent light through a
   material to be inspected; means for successively passing the light beam through different areas of the material to cover a large area and thereby develop successive side lobes, each successive side lobe being scanned by said photo diode linear array; means in said array for generating an end of scan signal, said series of counters being responsive to said end of scan signal to be reset so that said counters will provide successive pluralities of counts indicative of the amplitude envelope shape of the successive side lobes; storage means connected to the outputs of said counters to store successive pluralities of counts; computing means connected to said storage means for computing the mean values of counts from a succession of said pluralities stored therein; and comparison circuit means receiving said mean values and comparing the same with subsequently generated pluralities of counts and responsive to deviations of said subsequently generated pluralities of counts from said mean values by a given amount to provide a decision output signal indicative of a defect.

12. A system according to claim 10 including means for correlating the position of that spaced increment during which the voltage signal having the highest voltage value is provided with the beginning of said successively spaced increments to thereby provide an indication of the location of the peak amplitude of said side lobe.

13. A system according to claim 10 including means in said array for generating an end of scan signal; delay counter means connected between said source of fixed frequency clock pulses and said array start generator; means connected to said delay counter means responsive to the value of the voltage signal having the highest voltage value to vary said delay counter means in a manner to delay the generation of said start scan pulse by said array start generator after generation of said end of scan signal to expose the photo diodes in said array to said light lobe prior to the start of scanning to thereby vary the level of said voltage signals in response to a subsequent scanning of said diodes in a manner to substantially fill said voltage range defined by said reference voltages.

14. A system according to claim 10, in which said given period of time for analyzing the shape of the amplitude envelope of said light lobe is less than 150 microseconds.

* * * * *